US012716059B2

(12) United States Patent
Milczek et al.

(10) Patent No.: US 12,716,059 B2
(45) Date of Patent: Aug. 25, 2026

(54) IMMOBILIZED PROTEASES FOR ACTIVATION OF THE ZYMOGEN FORM OF TRANSGLUTAMINASE

(71) Applicant: Curie Co. Inc., Durham, NC (US)

(72) Inventors: Erika M. Milczek, Durham, NC (US); Robert Dicosimo, Doylestown, PA (US); Steven Walsh, Durham, NC (US); Malcolm McCray, Durham, NC (US)

(73) Assignee: Curie Co. Inc., Durham, NC (US)

( * ) Notice: Subject to any disclaimer, the term of this patent is extended or adjusted under 35 U.S.C. 154(b) by 420 days.

(21) Appl. No.: 17/930,965

(22) Filed: Sep. 9, 2022

(65) Prior Publication Data

US 2024/0093162 A1 Mar. 21, 2024

(51) Int. Cl.

| | |
|---|---|
| ***C12N 9/10*** | (2006.01) |
| ***C12N 9/48*** | (2006.01) |
| ***C12N 11/18*** | (2006.01) |

(52) U.S. Cl.

CPC ............. *C12N 9/1044* (2013.01); *C12N 9/48* (2013.01); *C12N 9/485* (2013.01); *C12N 11/18* (2013.01); *C12Y 203/02013* (2013.01)

(58) Field of Classification Search

CPC ......... C12N 9/1044; C12N 9/48; C12N 9/485
See application file for complete search history.

(56) References Cited

U.S. PATENT DOCUMENTS

2009/0004720 A1* 1/2009 Hua .................... C12N 9/0006 536/22.1

FOREIGN PATENT DOCUMENTS

| | | | |
|---|---|---|---|
| WO | WO 93/15234 | A1 | 8/1993 |
| WO | WO 2011/133704 | A2 | 10/2011 |
| WO | WO 2016/170447 | A1 | 10/2016 |
| WO | WO 2021/178001 | A1 | 9/2021 |
| WO | WO 2022/055902 | A2 | 3/2022 |

OTHER PUBLICATIONS

A0A3G4VZ98_9ACTN. UniProtKB/TrEMBL. Apr. 7, 2021.*

A0A3G4VPC7_9ACTN. UniProtKB/TrEMBL. Apr. 7, 2021.*

International Search Report and Written Opinion of the International Searching Authority for PCT/US2022/076202, May 2, 2023, 10 pages.

Wang et al., "New strategy for specific activation of recombinant microbial pro-transglutaminase by introducing an enterokinase cleavage site," Biotechnol Lett, Nov. 10, 2012, 35(3):383-388.

International Search Report and Written Opinion for International Application No. PCT/US2022/019738, Jul. 11, 2022, 14 pages.

Marx et al., "Purification and Activation of a Recombinant Histidine-Tagged Pro-Transglutaminase After Soluble Expression in *Escherichia coli* and Partial Characterization of the Active Enzyme," Enzyme and Microbial Technology, 2008, 42(7):568-575.

Naveed et al., "Protease-A Versatile and Ecofriendly Biocatalyst with Multi-Industrial Applications: An Updated Review," Catalysis Letters, 2020,151(2):307-323.

(Continued)

*Primary Examiner* — Yong D Pak

(74) *Attorney, Agent, or Firm* — Finnegan, Henderson, Farabow, Garrett & Dunner, LLP

(57) ABSTRACT

Immobilized proteases for activation of the zymogen form of transglutaminase are disclosed.

3 Claims, 2 Drawing Sheets

Figure 1:
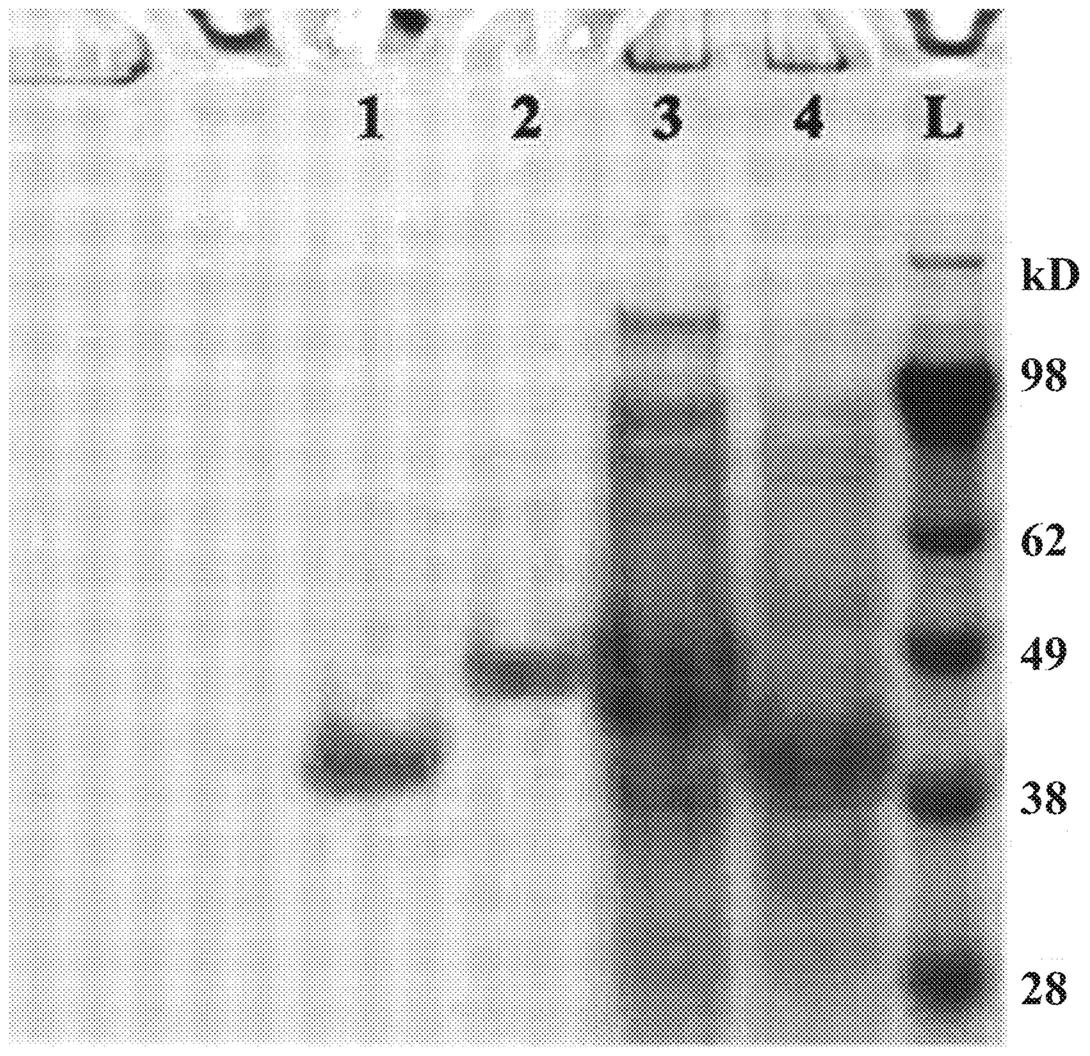

Specification includes a Sequence Listing.

(56) References Cited

OTHER PUBLICATIONS

Pasternack et al., "Bacterial pro-transglutaminase from Streptoverticillium mobaraense—purification, characterisation and sequence of the zymogen," Eur J Biochem, 1998, 257(3):570-576.
Yang et al., "Crystal structure and inhibition studies of transglutaminase from *Streptomyces mobaraense,*" J Biol Chem, 2011, 286(9):7301-7307.
Zhang et al., "Microbial transglutaminase production: understanding the mechanism," Biotechnol Genet Eng Rev, 2009, 26:205-221.
Zedira GmbH, "Zedira's MTG-Handbook," Edition 1.0, Feb. 2020, Chapter 2: "MTG—Structure and Numbers," pp. 4-7, 7 pages.
Zotzel et al., "Activated transglutaminase from *Streptomyces mobaraensis* is processed by a tripeptidy1 aminopeptidase in the final step," Eur J Biochem, 2003, 270(20):4149-4155.
Zotzel et al., "Transglutaminase from *Streptomyces mobaraensis* is activated by an endogenous metalloprotease," Eur J Biochem, 2003, 270(15):3214-3222.

* cited by examiner

IMMOBILIZED PROTEASES FOR ACTIVATION OF THE ZYMOGEN FORM OF TRANSGLUTAMINASE

INCORPORATION BY REFERENCE

The sequence listing provided in the file named Sequence-Listing.xml with a size of 8,587 bytes, which was created on Sep. 6, 2022 and which is filed herewith, is incorporated by reference in its entirety.

FIELD

The field pertains to immobilized proteases and, in particular, to immobilized proteases for activation of the zymogen form of transglutaminase.

BACKGROUND

Transglutaminases (Tgases, EC2.3.2.13) are a family of enzymes that catalyze crosslinking between the gamma-carboxamide group in glutamine residues (acyl donors) and a variety of primary amines (acyl acceptors), including the amino group of lysine. Tgases can be found throughout all groups of organisms including prokaryotes, eukaryotes, and plants. Tgases in animals, for example, include blood coagulation factor XIII, which is a multi-domain protein and depends on calcium for regulation of enzyme function. Microbial transglutaminases, on the other hand, have only a single domain and do not depend on calcium for activity, i.e., Tgases of microbial origin are calcium-independent. Thus, microbial Tgases represent a major advantage for their practical use.

Commercially available Tgase is produced by fermentation of *Streptomyces mobaraensis*. Tgase is expressed as an inactive zymogen having a pro-peptide sequence at the N-terminus of the mature domain. The active enzyme is produced by removing the pro-peptide by proteolytic processing in solution to afford the mature domain.

Zotsel, et al., Eur. J. Biochem., 270, 3214-3222 (2003) described activation of Tgase from *Streptomyces mobaraensis* by a Tgase-activating M4 metalloprotease (TAMEP) in soluble form, which cleaves the first 41 amino acids of the zymogen form of Tgase, i.e., pro-Tgase, between Ser41 and Phe42 (GPS-FRAP cleavage site, see SEQ ID NO:1).

Zotsel, et al., Eur. J. Biochem., 270, 4149-4155 (2003) further reported that TAMEP-activated Tgase has a N-terminal tetrapeptide (Phe-Arg-Ala-Pro), i.e., FRAP, which can be removed by a transglutaminase activating tripeptidyl aminopeptidase (TAP) from *Streptomyces mobaraensis* (SM-TAP) also in soluble form. SM-TAP cleaves between the Pro45 and Asp46 (FRAP-DSDD cleavage site, see SEQ ID NO:1) to afford mature, catalytically active Tgase, with FRAP removed, i.e., in a mature, catalytically active form.

Use of soluble enzymes during post-translational processing of the inactive zymogen of Tgase leads to complications in purification as this necessitates separation of multiple enzymes from a fermentation broth. Often this requires use of chromatographic purification resulting in increased manufacturing cost and complexity.

In contrast, immobilization of enzymes can be useful in improving the catalytic performance of enzymes and can aid in simplifying downstream processing. Immobilization facilitates re-use of enzymes, allows for an easy and more simplified recovery of both enzymes and products, allows continuous operations of enzymatic processes, rapid termination of reactions, and greater variety of bioreactor designs.

It has been shown through unpublished research that commercially available immobilized proteases are not suitable for producing mature, catalytically active Tgase, i.e., with the entire Pro sequence (including FRAP) removed. These commercially available immobilized proteases either cleave upstream of the desired amino acid position and/or over-digest the mature Tgase. Thus, there is a need for immobilized proteases that will produce a mature, catalytically active Tgase from a zymogen form by cleaving at the correct amino acid position, after the Pro45, while not over-digesting the mature enzyme.

An additional factor that complicates post-translational processing of zymogen form of Tgase to the mature, catalytically active Tgase form is that the native proteases, TAMEP and a TAP such as SM-TAP, used to activate Tgase in the zymogen form are deactivated by the catalytically active, mature Tgase and/or a catalytically active, not mature Tgase (i.e., FRAP-Tgase or Tgase having FRAP at its N-terminus).

Both TAMEP and SM-TAP are potentially substrates for mature, catalytically active Tgase or catalytically active, not mature Tgase, as they contain multiple glutamine and lysine residues, which may react with mature Tgase to form crosslinked products (Gln-Lys) or result in deamination of glutamine to glutamic acid (hydrolysis of Gln to Glu), thereby inactivating TAMEP and SM-TAP. This deactivation of TAMEP and SM-TAP leads to the incomplete conversion of the zymogen form of Tgase to mature, catalytically active Tgase by TAMEP and SM-TAP and further increases the cost and complexity in the purification and isolation of recombinantly expressed, mature, catalytically active Tgase or catalytically active, not mature Tgase Surprisingly, it was found that immobilizing a TAMEP and a TAP, either separately or together by co-protease immobilization as disclosed herein, both proteases have been found to be protected from Tgase catalyzed deactivation. This greatly simplifies downstream processing to obtain the mature, catalytically active Tgase and facilitates recombinant expression and purification of both wild-type and variants of Tgase.

Thus, there remains a need for immobilizing the proteases needed to produce a mature, catalytically active Tgase from its zymogen form. The disclosure herein addresses a long unmet need for immobilized protease that can facilitate the expression and purification of recombinantly expressed mature, catalytically active Tgase.

SUMMARY

In a first embodiment, there is disclosed a transglutaminase-activating M4 metalloprotease (TAMEP) immobilized on a porous solid support.

In a second embodiment, there is disclosed a transglutaminase-activating tripeptidyl aminopeptidase (TAP) immobilized on a porous solid support.

In a third embodiment, there is disclosed a transglutaminase-activating M4 metalloprotease (TAMEP) and a tripeptidyl aminopeptidase (TAP) co-immobilized on a porous solid support.

In a fourth embodiment, there is disclosed a method for activating a zymogen form of a transglutaminase or a variant thereof to produce a mature, catalytically active form of the transglutaminase, the method comprising a) immobilizing at least one transglutaminase-activating M4 metalloprotease (TAMEP) and/or at least one tripeptidyl aminopeptidase (TAP), provided that if both TAMEP and TAP are immobilized, the TAMEP and TAP are separately immobilized on the same or different porous solid support; and b) contacting the zymogen form of transglutaminase with TAMEP and TAP wherein at least one of TAMEP or TAP is immobilized to produce a mature, catalytically active form of the transglutaminase and further wherein if the contacting is sequential then TAMEP is contacted first.

Alternatively, step a) may comprise providing at least one TAMEP and/or at least one TAP immobilized on a porous solid support.

In a fifth embodiment, there is disclosed a method for activating a zymogen form of a transglutaminase or a variant thereof to produce a mature, catalytically active form of the transglutaminase, the method comprising a) co-immobilizing at least one transglutaminase-activating M4 metalloprotease (TAMEP) and at least one tripeptidyl aminopeptidase (TAP) on the same porous solid support; and b) contacting the zymogen form of transglutaminase with co-immobilized TAMEP and TAP to produce a mature, catalytically active form of the transglutaminase.

In a sixth embodiment, there is disclosed a method for activating a zymogen form of a transglutaminase or a variant thereof to produce a catalytically active, not mature form of the transglutaminase, the method comprising a) immobilizing at least one transglutaminase-activating M4 metalloprotease s(TAMEP) on a porous solid support, and b) contacting the zymogen form of transglutaminase with the immobilized at least one TAMEP to produce a catalytically active, not mature form of the transglutaminase.

Optionally, the catalytically active, not mature transglutaminase can be separated from at least one of the immobilized or co-immobilized proteases.

In still yet another aspect, for all the embodiments disclosed herein, preferably, the TAMEP is from *Streptomyces* sp. and, most preferably, the TAMEP is from *Streptomyces mobaraensis* and, preferably, the TAP is from *Streptomyces* sp. and, most preferably, the TAP is from *Streptomyces mobaraensis* (SM-TAP).

BRIEF DESCRIPTION OF THE DRAWINGS AND SEQUENCES

FIG. 1 shows SDS-PAGE analysis of *S. mobaraensis* Tgase variant as described in Example 1. Lane 1—mature Tgase secured from commercial sources; Lane 2—zymogen (pro-Tgase variant); Lane 3—clarified lysate containing zymogen (crude pro-Tgase variant); Lane 4—clarified lysate treated with immobilized protease for 60 minutes; Lane L—protein ladder. Expected molecular weight of the zymogen (pro-Tgase variant) is 43.6 kDa and the expected molecular weight of the mature Tgase variant is 38.9 kDa.

Figure 2:
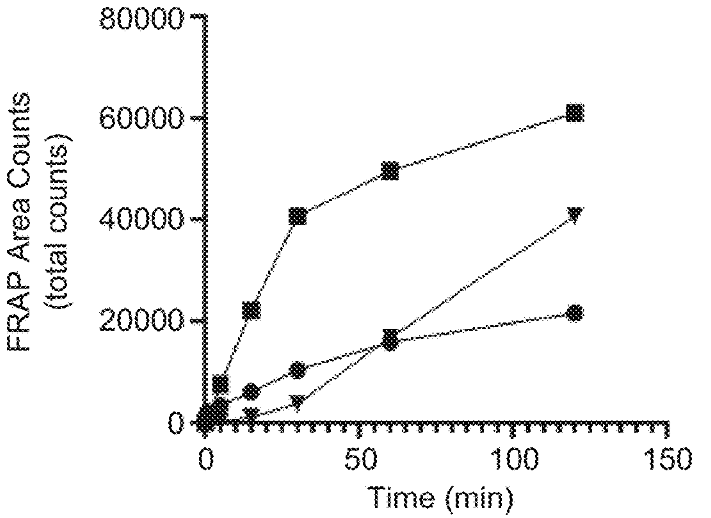

FIG. 2 shows the activity of TAMEP and SM-TAP co-immobilized on the same porous solid support, TAMEP and SM-TAP each immobilized on a different porous solid support, and TAMEP (soluble) with SM-TAP (soluble).

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.26 (2021) and the sequence listing requirements of the European Patent Convention(EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO:1 corresponds to the wild-type zymogen form of Tgase from *Streptomyces mobaraensis* (Pro-Tgase). Leader sequence (pro-) is denoted in bold, underlined text.

SEQ ID NO:2 corresponds to a thermostable variant of *Streptomyces mobaraensis* Tgase in zymogen form with two additional methionine residues—one methionine is located at the N-terminus of the Pro-sequence and the second methionine is located between the Pro-sequence and the N-terminus of the mature domain (Pro-Tgase variant). Leader sequence (pro-) is denoted in bold, underlined text.

SEQ ID NO:3 corresponds to wild-type *Streptomyces mobaraensis* transglutaminase-activating M4 metalloprotease (TAMEP) in zymogen form with the native signal peptide deleted and a leading methionine included to facilitate recombinant expression. Putative leader sequence (pro-) is denoted in bold, underlined text.

SEQ ID NO: 4 corresponds to the wild-type *Streptomyces mobaraensis* transglutaminase-activating tripeptidyl aminopeptidase (SM-TAP) in zymogen form with the native signal peptide deleted and a leading methionine included to facilitate recombinant expression. Putative leader sequence (pro-) is denoted in bold, underlined text.

SEQ ID NO: 5 corresponds to a thermostable variant of *Streptomyces mobaraensis* Tgase having a FRAP tetrapeptide at the N-terminal end with a methionine amino acid residue located between the FRAP tetrapeptide and the N-terminus of the mature domain of the thermostable Tgase variant (FRAP-Tgase variant). Leader sequence (pro-) is denoted in bold, underlined text.

SEQ ID NO: 6 corresponds to a thermostable variant of *Streptomyces mobaraensis* Tgase with the FRAP tetrapeptide removed from the N-terminus of the mature domain of the thermostable Tgase variant and a leading methionine amino acid residue is located at the N-terminus of the mature domain of the thermostable Tgase variant (thermostable Tgase variant).

DETAILED DESCRIPTION

All patents, patent applications, and publications cited herein are incorporated by reference in their entireties.

Words using the singular include the plural, and vice versa, unless the context clearly dictates otherwise.

In this disclosure, many terms and abbreviations are used. The following definitions apply unless specifically stated otherwise.

As used herein, the singular forms "a," "an," and "the" include plural references unless the context clearly dictates otherwise. For example, the term "a compound" or "at least one compound" may include a plurality of compounds, including mixtures thereof. The terms "a," "an," "the," "one or more," and "at least one," for example, can be used interchangeably herein.

The term "about" as used herein can allow for a degree of variability in a value or range, for example, within 10%, within 5%, or within 1% of a stated value or of a stated limit of a range.

The terms "and/or" and "or" are used interchangeably herein and refer to a specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B and/or C" is intended to encompass each of the following aspects: "A, B and C"; "A, B or C"; "A or C"; "A or B"; "B or C"; "A and C"; "A and B"; "B and C"; "A" (alone); "B" (alone); and "C" (alone).

The terms "comprises," "comprising," "includes," "including," "having," and their conjugates are used interchangeably and mean "including but not limited to." It is understood that wherever aspects are described herein with the language "comprising," otherwise analogous aspects described in terms of "consisting of" and/or "consisting essentially of" are also provided.

The term "consisting of" means "including and limited to."

The term "consisting essentially of" means that a composition, formulation, or method includes any listed component, ingredient or steps and is open to unlisted components, ingredients or steps that do not materially affect the basic characteristics of the composition, formulation, or method.

Throughout this application, various embodiments can be presented in a range format. It should be understood that the description in range format is merely for convenience and brevity and should not be construed as an inflexible limitation on the scope of the embodiments described herein. Accordingly, the description of a range should be considered to have specifically disclosed all the possible subranges as well as individual numerical values within that range. For example, description of a range, such as from 1 to 6 should be considered to have subranges such as from 1 to 2, from 1 to 3, from 1 to 4 and from 1 to 5, from 2 to 3, from 2 to 4, from 2 to 5, from 2 to 6, from 3 to 4, from 3 to 5, from 3 to 6, etc., as well as individual numbers within that range, for example, 1, 2, 3, 4, 5 and 6. This applies regardless of the breadth of the range.

"Optional" or "optionally" means that the subsequently described event, circumstance, or material may or may not occur or be present, and that the description includes instances where the event, circumstance, or material occurs or is present and instances where it does not occur or is not present.

The term "immobilized" as used herein means a technical process in which molecule, such as an enzyme, is fixed to or within a solid support. This can be achieved by a variety of techniques including, but not limited to, covalent binding/attachment, ionic bonding, entrapment, or adsorption.

The term "co-immobilized" means that at least two distinct molecules, such as at least two different enzymes, are fixed to or within the same solid support.

The term "solid support" refers to a range of materials, either biological, non-biological, organic, inorganic, or a combination of any of these. Thus, a solid support may be of any suitable composition to which the molecule to be attached may be applied.

The term "porous solid support" as used herein means simply any solid containing void space(s), i.e., space not occupied by the main framework of atoms that make up the structure of the solid. Examples of such supports include, but are not limited to, polyacrylate, polymethacrylate, polystyrene, etc. that can be modified with a functional group. For example, polymethacrylate can be modified with epoxide functional groups or primary amine groups capable of being activated by a crosslinking agent. Examples of such functional groups, include but are not limited to, epoxide, alkyl, phenyl, sulphonic, amines (primary, secondary, tertiary or quaternary), etc.

Other examples of porous solid supports include, but are not limited to, aminopropylsilated controlled pore glass ("CPG"), diatomaceous earth or metal-organic frameworks ("MOFS").

Preferably, the porous solid support is selected from any of the supports set forth in Table 2 in the Examples below. Examples of suitable porous solid supports include, but are not limited to, IB-COV-1, IB-COV-2, IB-COV-3, IB-ADS-1, IB-ADS-2, IB-ADS-3, IB-ADS-4, IB-CAT-1, IB-ANI-1, IB-ANI-2, IB-ANI-3, IB-ANI-4, ECR8204F, ECR8209F, AND ECR8215F.

The terms "covalently bound" or "covalent bond" refers to a chemical bond involving the sharing of electron pairs between atoms. These electron pairs are known as shared pairs or bonding pairs, and the stable balance of attractive and repulsive forces between atoms, when they share electrons is known as covalent bonding. By way of example, the pro and mature domains may be covalently bound via a peptide bond.

The term "ionic bond" may also be referred to as an electrovalent bond. It is a type of linkage formed from the electrostatic attraction between oppositely charged ions in a chemical compound. Such a bond forms when the valence (outermost) electrons of one atom are transferred permanently to another atom. The atom that loses the electrons becomes a positively charged ion, i.e., a cation, while the one that gains the electrons becomes a negatively charged ion, i.e., an anion. An ionic bond is one example of a non-covalent bond.

The term "non-covalently bound" differs from covalently bound in that non-covalent binding does not involve the sharing of electrons between atoms. Thus, non-covalent binding can occur by completely exchanging electrons between atoms or by not exchanging electrons at all. Non-covalent bonds tend to be weaker than covalent bonds. Types of non-covalent bonds include but are not limited to ionic bonds, hydrogen bonds and Van der Waals interactions.

The term "adsorption" as used herein refers to a process that involves the accumulation of a substance or molecular species in higher concentrations on a surface, i.e., the adhesion of atoms, ions, or molecules from a gas, liquid, or dissolved solid to a surface. Adsorption can include, but is not limited to interactions such a hydrophobic or hydrophilic interactions.

The terms "zymogen" and "proenzyme" are used interchangeably herein and refer to an inactive precursor of an enzyme, which may be converted into an active or mature enzyme by post-translational modification, for example, by catalytic action, such as via proteolytic cleavage of a pro-peptide sequence.

The terms "pro-peptide," "pro-domain," "pro-sequence," and "pro-region" are used interchangeably herein and refer to a N-terminal peptide leader sequence (including the FRAP tetrapeptide) that, when fully cleaved, produces a mature, catalytically active Tgase. However, if the full pro-peptide is not cleaved such that it does not include FRAP (i.e., FRAPless pro-peptide) then a catalytically active, not mature Tgase is produced.

The pro-peptide can be regarded as serving a regulatory function while the mature domain serves a catalytic function. Pro-peptides generally are recognized to have four major functions: 1) pro-peptides can function as intramolecular chaperones or folding assistants by determining the three-dimensional structure of a protein; 2) pro-peptides can function as inhibitors or activation peptides; 3) pro-peptides can direct protein sorting into specific cellular compartments or extra-cellular space and 4) pro-peptides can mediate the precursor interaction with other molecules (such as peptides, proteins, and polysaccharides) or supramolecular structures (e.g., cell walls). A single pro-peptide can perform several or even all these functions.

The term "transglutaminase" (Tgase, EC2.3.2.13) refers to a family of enzymes that catalyze the formation of an isopeptide bond between a primary amine, for example, the ε-amine of a lysine molecule, and the acyl group of a protein- or peptide-bound glutamine. Transglutaminases may catalyze a transamidation reaction between glutamyl and lysyl side chains of target proteins. Proteins possessing Tgase activity have been found in microorganisms, plants, and animals. Tgases are widely distributed in various organs, tissues, and bodily fluids. Tgases also form extensively cross-linked, generally insoluble, protein biopolymers that are needed for an organism to create barriers and stable structures.

Tgases of microbial origin, unlike eukaryotic Tgases, are calcium-independent, which represents a major advantage for their practical use. "Microbial transglutaminase" is one of the most extensively studied industrial enzymes for protein functionalization and protein crosslinking because of its ability to polymerize or functionalize proteins through the formation of a stable ε-(γ-glutamyl)lysine isopeptide bond without the constraint of a consensus sequence or additional cofactors. Microbial Tgase is a subset of Tgases.

The most commonly used Tgase is microbial transglutaminase from *Streptomyces mobaraensis*, the wild-type zymogen form (Pro-Tgase) having the amino acid sequence corresponding to SEQ ID NO:1. The terms "Pro-Tgase" and "zymogen form of Tgase" are used interchangeably herein. It has been known that Tgase from *Streptomyces mobaraensis* is secreted in a zymogen form, i.e., Pro-Tgase. Activation of the zymogen form of Tgase (Pro-Tgase) occurs in two steps. First, the pro-peptide is cleaved from the N-terminal end of the Pro-Tgase by a transglutaminase-activating M4 metalloprotease ("TAMEP"). Some TAMEPs produce a catalytically active, not mature Tgase leaving a FRAP tetrapeptide at the N-terminal end of Tgase (i.e., FRAP-Tgase). Some TAMEPs produce catalytically active, not mature Tgase having a partial FRAP peptide such as RAP, AP, or P attached to the N-terminal end of the Tgase. In other words, the resulting pro-peptide does not contain the FRAP-tetrapeptide, i.e., it is a FRAPless pro-peptide. The N-terminal FRAP tetrapeptide on the Tgase, or what remains of it, can then be subsequently cleaved by using a transglutaminase tripeptidyl aminopeptidase ("TAP") to produce a mature, catalytically active, Tgase having no FRAP. For clarity, the terms "mature, catalytically active," and "catalytically active, mature" are used interchangeably herein. Similarly, the terms "not mature, catalytically active" and "catalytically active, not mature" are used interchangeably herein.

Transglutaminase variants and methods of producing such variants are disclosed, for example, in PCT Publication Numbers WO 2016/170447, published on Oct. 27, 2016, and WO 2019/094301, published on May 16, 2019.

A "protease" (also called a peptidase or proteinase) refers to enzymes capable of cleaving peptide bonds. Proteases are any of various enzymes, such as endopeptidases and exopeptidases, that catalyze the hydrolytic breakdown of proteins into peptides and amino acids. Proteases can be classified into seven broad groups: serine proteases, cysteine proteases, threonine proteases, aspartic proteases, glutamic proteases, metalloproteases, and asparagine peptide lyases. Proteases can be found in animals, plants, bacteria, fungi, archaea, and viruses. The terms "protease," "peptidase," and "proteinase" are used interchangeably herein.

The term "amino acid" refers to the basic chemical structural unit of a protein, peptide, or polypeptide. The following abbreviations used herein to identify specific amino acids can be found in Table 1.

TABLE 1

One- and Three-Letter Amino Acid Abbreviations

| Amino Acid | Three-Letter Abbreviation | One-Letter Abbreviation |
|---|---|---|
| Alanine | Ala | A |
| Arginine | Arg | R |
| Asparagine | Asn | N |
| Thermostable serine acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

The terms "peptides," "proteins," and "polypeptides" are used interchangeably herein and refer to a polymer of amino acids joined together by peptide bonds. A "protein" or "polypeptide" comprises a polymeric sequence of amino acid residues. The single and 3-letter codes for amino acids as defined in conformity with the IUPAC-IUB Joint Commission on Biochemical Nomenclature (JCBN) are used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S." When describing modifications, a position followed by amino acids listed in parentheses indicates a list of modifications at that position by any of the listed amino acids. For example, 6 (L, I) means position 6 can be substituted with a leucine or isoleucine. At times, in a sequence, a slash (/) is used to define modifications, e.g., F/V, indicates that the position may have a phenylalanine or valine at that position.

One of ordinary skill in the art will appreciate that modifications of amino acid sequences disclosed herein can be made while retaining the function associated with the disclosed amino acid sequences. For example, it is well known in the art that alterations in a gene at a given site which result in the production of a chemically equivalent amino acid, but do not affect the functional properties of the encoded protein, are common.

The term "mutation" herein refers to a change introduced into a parental sequence, including, but not limited to, modifications such as insertions or deletions (including truncations), thereby producing a "variant." The consequences of a mutation include, but are not limited to, the creation of a new character, property, function, phenotype, or trait not found in the protein encoded by the parental sequence.

Related (and derivative) proteins encompass "variant," "mutant," or "modified" proteins, which terms are used interchangeably herein. Variant (i.e., mutant or modified) proteins differ from another (i.e., parental) protein or from one another due to modifications in one or more amino acid residues. For example, a variant may include one or more amino acid modifications such as one or more amino acid deletions/truncations, insertions, or substitutions as compared to the parental protein from which it is derived.

Alternatively or additionally, variants may have a specified degree of sequence identity with a reference protein or nucleic acid, e.g., as determined using a sequence alignment tool, such as BLAST, ALIGN, and CLUSTAL. For example, variant proteins or nucleic acids may have at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid or nucleic acid sequence identity with a reference sequence and integer percentage therebetween.

As used herein, with regard to amino acid residue positions, "corresponding to," "corresponds substantially to," "corresponding substantially to," "correspond to," or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

One of ordinary skill in the art will appreciate that modifications of amino acid sequences disclosed herein can be made while retaining the function associated with the disclosed amino acid sequences. For example, it is well known in the art that alterations in a gene which result in the production of a chemically equivalent amino acid at a given site, but do not affect the functional properties of the encoded protein, are common.

Related (and derivative) proteins encompass "variant" or "mutant" proteins, which terms are used interchangeably herein. Variant proteins differ from another (i.e., parental) protein and/or from one another by a small number of amino acid residues. A variant may include one or more amino acid mutations (e.g., amino acid deletion, insertion or substitution) as compared to the parental protein from which it is derived. Alternatively, or additionally, variants may have a specified degree of sequence identity with a reference protein or nucleic acid, e.g., as determined using a sequence alignment tool, such as BLAST, ALIGN, and CLUSTAL. For example, variant proteins or nucleic acid may have at least about 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or even 99.5% amino acid sequence or nucleic acid identity with a reference sequence and integer percentage therebetween The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant/engineered nucleic acids and protein sequences produced in the laboratory or modification of the wild-type sequence).

The term "derived from" encompasses the terms "originated from," "obtained from," "obtainable from," "isolated from," "purified from," and "created from," and generally indicates that one specified material finds its origin in another specified material or has features that can be described with reference to another specified material.

The terms "isolated," "purified," "separated," and "recovered" as used herein refer to a material (e.g., a protein, nucleic acid, or cell) that is removed from at least one component with which it is naturally associated. For example, these terms may refer to a material which is substantially or essentially free from components which normally accompany it as found in its native state, such as, for example, an intact biological system. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

In a first embodiment, there is disclosed a transglutaminase-activating M4 metalloprotease ("TAMEP") immobilized on a porous solid support.

With regard to immobilized TAMEP, the preferred solid support is a porous solid support as described above. Any porous solid support to which TAMEP can be immobilized can be used. It may be pretreated or functionalized prior to application of the TAMEP to facilitate binding, or for any other desired purpose, such as fostering conditions favorable for activity or any other desired property or to avoid undesired interactions with other entities. Many such surface treatments and/or functionalizations are known in the art and selection of a suitable treatment and/or functionalization will depend upon the TAMEP and upon the attendant conditions and desired activity. Examples of such supports include, but are not limited to, polyacrylate, polymethacrylate, polystyrene, etc. that can be modified with a functional group. For example, polymethacrylate can be modified with epoxide functional groups or primary amine groups capable of being activated by a crosslinking agent. Examples of such functional groups, include but are not limited to, epoxide, alkyl, phenyl, sulphonic, amines (primary, secondary, tertiary or quaternary), etc.

Other examples of porous solid supports include, but are not limited to, aminopropylsilated controlled pore glass ("CPG"), diatomaceous earth or metal-organic frameworks ("MOFS").

Preferably, the porous solid support is selected from any of the supports set forth in Table 2 in the Examples. Examples of suitable porous solid supports include, but are not limited to, IB-COV-1, IB-COV-2, IB-COV-3, IB-ADS-1, IB-ADS-2, IB-ADS-3, IB-ADS-4, IB-CAT-1, IB-ANI-1, IB-ANI-2, IB-ANI-3, IB-ANI-4, ECR8204F, ECR8209F, AND ECR8215F.

The terms "active TAMEP" and "TAMEP" are used interchangeably herein. If TAMEP is made in a zymogen form, then active TAMEP is made by removal of that portion of the N-terminus from the zymogen form needed to produce active enzyme. TAMEP can be immobilized using any of methods of attachment discussed above and, in the Examples below, namely, by means of covalent bonds, ionic bonds, or adsorption. Preferably, TAMEP is immobilized using covalent bonds. Alternatively, it is believed that TAMEP in a zymogen form may also be immobilized and subsequently activated.

TAMEP can be obtained from a variety of microbial sources, including, but not limited to, *Streptomyces* sp. Non-limiting examples include *Streptomyces mobaraensis, Streptomyces huiliensis, Streptomyces* sp. TYQ1024, *Streptomyces abikoensis, Streptomyces hiroshimensis, Streptomyces albireticuli, Streptomyces triculaminicus, Streptomyces olivoverticillatus, Streptomyces luteoverticillatus, Streptomyces cinnamoneus, Streptomyces caatingaensis, Streptomyces roseoverticillatus, Streptomyces griseocarneus, Streptomyces rectiverticillatus, Streptomyces roseifaciens, Streptomyces eurocidicus, Streptomyces klenkii, Streptomyces netropsis, Streptomyces hygroscopicus, Streptomyces varsoviensis*, and the like. Preferably, TAMEP is obtained from *Streptomyces mobaraensis.*

SEQ ID NO:3 corresponds to the wild-type *Streptomyces mobaraensis* transglutaminase-activating M4 metalloprotease (TAMEP) in zymogen form with the native signal peptide deleted and a leading methionine included to facilitate recombinant expression. The putative leader sequence (pro-) is denoted in bold, underlined text and provided as amino acids 2 to 197 of SEQ ID NO: 3. Active TAMEP is produced by removal (such as by endogenous protease activity) of that portion of the N-terminus of the zymogen form needed to produce active enzyme. In the case of TAMEP, it is believed that the portion of the N-terminus of the zymogen form needed to produce active enzyme might involve removal of the identified putative pro region or a variant thereof from SEQ ID NO:3 to produce active TAMEP.

Thus, it appears there may be active TAMEPs that might share at least 70% sequence identity with an active form of the amino acid sequence set forth in SEQ ID NO:3. Even more preferably, TAMEP from *Streptomyces mobaraensis* comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or even 99.5% amino acid sequence identity with the active form (without the putative leader sequence or a variant thereof) of the amino acid sequence set forth in SEQ ID NO:3. Most preferably, TAMEP from *Streptomyces mobaraensis* comprises a sequence consisting essentially of the active form of the amino acid sequence set forth in SEQ ID NO:3.

The sequence of TAMEP after the putative leader sequence is removed from the zymogen form corresponds to amino acids 198 to 728 of SEQ ID NO: 3. The sequence of TAMEP after the leader sequence is removed from the zymogen form may correspond to one of the following ranges of amino acids of SEQ ID NO: 3: 182 to 728; 183 to 728; 184 to 728; 185 to 728; 186 to 728; 187 to 728; 188 to 728; 189 to 728; 190 to 728; 191 to 728; 192 to 728; 193 to 728; 194 to 728; 195 to 728; 196 to 728; 197 to 728; 198 to 728; or a variation thereof. Alternatively, the sequence of TAMEP after the leader sequence is removed from the zymogen form may correspond to one of the following ranges of amino acids of SEQ ID NO: 3: 199 to 728; 200 to 728; 201 to 728; 202 to 728; 203 to 728; 204 to 728; 205 to 728; 206 to 728; 207 to 728; 208 to 728; 209 to 728; 210 to 728; 211 to 728; 212 to 728; 213 to 728; 214 to 728; or a variation thereof.

The sequence of active TAMEP may correspond to one of the following ranges of amino acids of SEQ ID NO: 3: 182 to 728; 183 to 728; 184 to 728; 185 to 728; 186 to 728; 187 to 728; 188 to 728; 189 to 728; 190 to 728; 191 to 728; 192 to 728; 193 to 728; 194 to 728; 195 to 728; 196 to 728; 197 to 728; 198 to 728; or a variation thereof. Alternatively, the sequence of active TAMEP may correspond to one of the following ranges of amino acids of SEQ ID NO: 3: 199 to 728; 200 to 728; 201 to 728; 202 to 728; 203 to 728; 204 to 728; 205 to 728; 206 to 728; 207 to 728; 208 to 728; 209 to 728; 210 to 728; 211 to 728; 212 to 728; 213 to 728; 214 to 728; or a variation thereof.

In a second embodiment, there is disclosed a transglutaminase-activating tripeptidyl aminopeptidase ("TAP") immobilized on a porous solid support.

With regard to immobilized TAP, the preferred solid support is a porous solid support as described above. Any porous solid support to which TAP can be immobilized can be used. It may be pretreated or functionalized prior to application of the TAP to facilitate binding, or for any other desired purpose, such as fostering conditions favorable for activity or any other desired property or to avoid undesired interactions with other entities. Many such surface treatments and/or functionalizations are known in the art and selection of a suitable treatment and/or functionalization will depend upon the TAP and upon the attendant conditions and desired activity. Examples of such supports include, but are not limited to, polyacrylate, polymethacrylate, polystyrene, etc. that can be modified with a functional group. For example, polymethacrylate can be modified with epoxide functional groups or primary amine groups capable of being activated by a crosslinking agent. Examples of such functional groups, include but are not limited to, epoxide, alkyl, phenyl, sulphonic, amines (primary, secondary, tertiary or quaternary), etc.

Other examples of porous solid supports include, but are not limited to, aminopropylsilated controlled pore glass ("CPG"), diatomaceous earth or metal-organic frameworks ("MOFS").

Preferably, the porous solid support is selected from any of the supports set forth in Table 2 in the Examples. Examples of suitable porous solid supports include, but are not limited to, IB-COV-1, IB-COV-2, IB-COV-3, IB-ADS-1, IB-ADS-2, IB-ADS-3, IB-ADS-4, IB-CAT-1, IB-ANI-1, IB-ANI-2, IB-ANI-3, IB-ANI-4, ECR8204F, ECR8209F, AND ECR8215F.

Active TAP (i.e., not in a zymogen form) can be immobilized using any of methods of attachment discussed above and, in the Examples below, namely, by means of covalent bonds, ionic bonds, or adsorption. Preferably, TAP is immobilized using covalent bonds. Alternatively, it is believed that TAP in a zymogen form may also be immobilized and subsequently activated.

The terms "active TAP" and "TAP" are used interchangeably herein. If TAP is made in a zymogen form, then active TAP, is made by removal of that portion of the N-terminus from the zymogen form needed to produce active enzyme, TAP can be obtained from a variety of microbial sources, including, but not limited to, *Streptomyces* sp. Non-limiting examples include *Streptomyces mobaraensis, Streptomyces huiliensis, Streptomyces caatingaensis, Streptomyces abikoensis, Streptomyces olivoverticillatus, Streptomyces, luteoverticillatus, Streptomyces cinnamoneus, Streptomyces netropsis, Streptomyces eurucidicus, Streptomyces morookaense, Streptomyces hiroshimensis, Streptomyces roseifaciens, Streptomyces roseoverticillatus, Streptomyces hygroscopicus*, and the like. Preferably, TAP is obtained from *Streptomyces mobaraensis*. Preferably, TAP is obtained from *Streptomyces mobaraensis.*

SEQ ID NO: 4 corresponds to the wild-type *Streptomyces mobaraensis* transglutaminase-activating tripeptidyl aminopeptidase (SM-TAP) in zymogen form with the native signal peptide deleted and a leading methionine included to facilitate recombinant expression. Putative leader sequence (pro-)

is denoted in bold, underlined text and provided as amino acids 2 to 7 of SEQ ID NO: 4. Active TAP is produced by removal of that portion of the N-terminus of the zymogen form needed to produce active enzyme. In the case of TAP, it is believed that the portion of the N-terminus of the zymogen form needed to produce active enzyme might involve removal of the identified putative pro region or a variant thereof from SEQ ID NO:4 to produce active TAP.

Thus, it appears there may be active TAPs that might share at least 70% sequence identity with an active form of the amino acid sequence set forth in SEQ ID NO:4. Even more preferably, TAP is obtained from *Streptomyces mobaraensis* comprises a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or even 99.5% amino acid sequence identity with an active form (without the putative leader sequence or a variant thereof) of the amino acid sequence set forth in SEQ ID NO:4. Most preferably, TAP from *Streptomyces mobaraensis* comprises a sequence consisting essentially of an active form of the amino acid sequence set forth in SEQ ID NO:4.

The sequence of TAP after the putative leader sequence is removed from the zymogen form corresponds to amino acids 8 to 451 of SEQ ID NO: 4. The sequence of TAP after the leader sequence is removed from the zymogen form may correspond to one of the following ranges of amino acids of SEQ ID NO: 4: 2 to 451; 3 to 451; 4 to 451; 5 to 451; 6 to 451; 7 to 451; or 8 to 451; or a variation thereof. Alternatively, the sequence of TAP after the leader sequence is removed from the zymogen form may correspond to one of the following ranges of amino acids of SEQ ID NO: 4: 9 to 451; 10 to 451; 11 to 451; 12 to 451; 13 to 451; 14 to 451; 15 to 451; 16 to 451; 17 to 451; 18 to 451; 19 to 451; or 20 to 451; or a variant thereof.

The sequence of active TAP may correspond to one of the following ranges of amino acids of SEQ ID NO: 4: 2 to 451; 3 to 451; 4 to 451; 5 to 451; 6 to 451; 7 to 451; or 8 to 451; or a variation thereof. Alternatively, the sequence of active TAP may correspond to one of the following ranges of amino acids of SEQ ID NO: 4: 9 to 451; 10 to 451; 11 to 451; 12 to 451; 13 to 451; 14 to 451; 15 to 451; 16 to 451; 17 to 451; 18 to 451; 19 to 451; or 20 to 451; or a variant thereof.

In a third embodiment, both TAMEP and TAP (active form of each protease) can be co-immobilized on any of the porous solid supports disclosed herein. TAMEP and TAP are discussed in greater detail hereinabove. TAMEP and TAP can be co-immobilized using any of methods of attachment discussed above and in the Examples below, namely, by means of covalent bonds, ionic bonds, or adsorption. The preferred means of co-immobilization is by covalent bonds.

As is shown in Example 8 below, co-immobilized TAMEP and SM-TAP, and separately immobilized TAMEP and SM-TAP, outperformed soluble TAMEP and soluble SM-TAP. In addition, it was found, surprisingly and unexpectedly, that by immobilizing TAMEP and SM-TAP separately or co-immobilizing TAMEP and SM-TAP, as disclosed herein, these proteases appear to have been protected from deactivation by the mature, catalytically active Tgase or catalytically active, not mature Tgase. This greatly simplifies downstream processing to obtain the mature, catalytically active Tgase or catalytically active, not mature Tgase and facilitates recombinant expression and purification of both wild-type and variants of Tgase.

In a fourth embodiment, there is disclosed a method for activating a zymogen form of a transglutaminase or a variant thereof to produce a mature, catalytically active form of the transglutaminase, the method comprising a) immobilizing at least one transglutaminase-activating M4 metalloprotease (TAMEP) and/or at least one tripeptidyl aminopeptidase (TAP), provided that if both TAMEP and TAP are immobilized, the TAMEP and TAP are separately immobilized on the same or different porous solid support; and
b) contacting the zymogen form of transglutaminase with TAMEP and TAP, wherein at least one of TAMEP or TAP is immobilized, to produce a mature, catalytically active form of the transglutaminase.

Alternatively, step a) may comprise providing at least one TAMEP and/or at least one TAP immobilized on a porous solid support.

Optionally, the mature, catalytically active form of the transglutaminase is separated from the at least one of the immobilized proteases. Preferably, the at least one TAMEP is from *Streptomyces* sp. and the at least one TAP is from *Streptomyces* sp. Most preferably, the at least one TAMEP is from *Streptomyces mobaraensis* and the at least one TAP is from *Streptomyces mobaraensis*.

In a fifth embodiment, there is disclosed a method for activating a zymogen form of a transglutaminase or a variant thereof to produce a mature, catalytically active form of the transglutaminase, the method comprising a) co-immobilizing at least one transglutaminase-activating M4 metalloprotease (TAMEP) and at least one tripeptidyl aminopeptidase from (TAP) on the same porous solid support; and
b) contacting the zymogen form of transglutaminase with co-immobilized TAMEP and TAP to produce a mature, catalytically active form of the transglutaminase.

Optionally, the mature, catalytically active transglutaminase is separated from the at least one of the immobilized proteases. Preferably, the at least one TAMEP is from *Streptomyces* sp. and the at least one TAP is from *Streptomyces* sp. Most preferably, the at least one TAMEP is from *Streptomyces mobaraensis* and the at least one TAP is from *Streptomyces mobaraensis*.

In a sixth embodiment, there is disclosed a method for activating a zymogen form of a transglutaminase or a variant thereof to produce a catalytically active, not mature form of the transglutaminase, the method comprising a) immobilizing at least one transglutaminase-activating M4 metalloprotease (TAMEP) on a porous solid support; and
b) contacting the zymogen form of transglutaminase with immobilized at least one TAMEP to produce a catalytically active, not mature form of the transglutaminase.

Optionally, the catalytically active, not mature transglutaminase is separated from the at least one of the immobilized TAMEP. Preferably, the TAMEP is from *Streptomyces* sp. Most preferably, the TAMEP is from *Streptomyces mobaraensis*.

Any means of immobilization and co-immobilization discussed herein can be used to practice any the embodiments disclosed herein. The preferred means of immobilization or co-immobilization is by covalent bonds.

TAMEP and TAP are discussed in detail above.

Non-limiting embodiments of the foregoing disclosed herein include:

1. A transglutaminase-activating M4 metalloprotease (TAMEP) immobilized on a porous solid support.
2. The immobilized TAMEP of embodiment 1 wherein the TAMEP is from *Streptomyces* sp.

3. The immobilized TAMEP of embodiments 1 or 2 wherein the TAMEP is from *Streptomyces mobaraensis*.
4. A transglutaminase-activating tripeptidyl aminopeptidase from (TAP) immobilized on a porous solid support.
5. The immobilized TAP of embodiment 4 wherein the TAP is from *Streptomyces* sp.
6. The immobilized TAP of embodiments 4 or 5 wherein the TAP is from *Streptomyces mobaraensis* (SM-TAP).
7. A transglutaminase-activating M4 metalloprotease (TAMEP) and a tripeptidyl aminopeptidase (TAP) co-immobilized on a porous solid support.
8. The co-immobilized TAMEP and TAP of embodiment 7 wherein the TAMEP is from *Streptomyces* sp. and the TAP is from *Streptomyces* sp.
9. The co-immobilized TAMEP and TAP of embodiments 7 or 8 wherein the TAMEP is from *Streptomyces mobaraensis* and the TAP is from *Streptomyces mobaraensis*.
10. A method for activating a zymogen form of a transglutaminase or a variant thereof to produce a mature, catalytically active form of the transglutaminase, the method comprising
    a) immobilizing at least one transglutaminase-activating M4 metalloprotease (TAMEP) and/or at least one tripeptidyl aminopeptidase from (TAP), provided that if both TAMEP and TAP are immobilized, the TAMEP and TAP are separately immobilized on the same or different porous solid support, or providing at least one TAMEP and/or at least one TAP immobilized on a porous solid support; and
    b) contacting the zymogen form of transglutaminase with TAMEP and TAP, wherein at least one of TAMEP or TAP is immobilized, to produce a mature, catalytically active form of the transglutaminase.
11. The method of embodiment 10 wherein the mature, catalytically active form of transglutaminase is separated from the at least one of the immobilized proteases.
12. The method of embodiments 10 or 11 wherein the TAMEP is from *Streptomyces* sp. and the TAP is from *Streptomyces* sp.
13. The method of embodiments 10, 11, or 12 wherein the TAMEP is from *Streptomyces mobaraensis* and the TAP is from *Streptomyces mobaraensis*.
14. A method for activating a zymogen form of a transglutaminase or a variant thereof to produce a mature, catalytically active form of a transglutaminase, the method comprising
    a) co-immobilizing at least one transglutaminase-activating M4 metalloprotease (TAMEP) and at least one tripeptidyl aminopeptidase from (TAP) on the same porous solid support; and
    b) contacting the zymogen form of transglutaminase with co-immobilized TAMEP and TAP to produce a mature, catalytically active form of the transglutaminase.
15. The method of embodiment 14 wherein the mature, catalytically active transglutaminase is separated from the at least one of the immobilized proteases.
16. The method of embodiments 14 or 15 wherein the TAMEP is from *Streptomyces* sp. and the TAP is from *Streptomyces* sp.
17. The method of embodiments 14, 15, or 16 wherein the TAMEP is from *Streptomyces mobaraensis* and the TAP is from *Streptomyces mobaraensis*.

18. A method for activating a zymogen form of a transglutaminase or a variant thereof to produce a catalytically active, not mature form of a transglutaminase, the method comprising
    a) immobilizing at least one transglutaminase-activating M4 metalloprotease (TAMEP) on a same porous solid support; and
    b) contacting the zymogen form of transglutaminase with immobilized at least one TAMEP to produce a catalytically active, not mature form of the transglutaminase.
19. The method of embodiment 18 wherein the catalytically active, not mature transglutaminase is separated from the at least one of the immobilized TAMEP.
20. The method of embodiments 18 or 19 wherein the TAMEP is from *Streptomyces* sp.
21. The method of embodiments 18, 19, or 20 wherein the TAMEP is from *Streptomyces mobaraensis*.
22. The immobilized and co-immobilized TAMEP and methods of embodiments 1-3 or 7-21, wherein the TAMEP is the active form of TAMEP having the sequence in SEQ ID NO: 3.
23. The immobilized and co-immobilized TAMEP and methods of embodiments 1-3 or 7-21, wherein the TAMEP has a sequence comprising amino acids 182 to 728, 183 to 728, 184 to 728, 185 to 728, 186 to 728, 187 to 728, 188 to 728, 189 to 728, 190 to 728, 191 to 728, 192 to 728, 193 to 728, 194 to 728, 195 to 728, 196 to 728, 197 to 728, 198 to 728, 199 to 728, 200 to 728, 201 to 728, 202 to 728, 203 to 728, 204 to 728, 205 to 728, 206 to 728, 207 to 728, 208 to 728, 209 to 728, 210 to 728, 211 to 728, 212 to 728, 213 to 728, or 214 to 728 of SEQ ID NO: 3.
24. The immobilized and co-immobilized TAP and methods of embodiments 4-6 or 7-21, wherein the TAP is the active form of TAP having the sequence in SEQ ID NO: 4.
25. The immobilized and co-immobilized TAP and methods of embodiments 4-6 or 7-21, wherein the TAP has a sequence comprising amino acids 2 to 451, 3 to 451, 4 to 451, 5 to 451, 6 to 451, 7 to 451, or 8 to 451, 9 to 451, 10 to 451, 11 to 451, 12 to 451, 13 to 451, 14 to 451, 15 to 451, 16 to 451, 17 to 451, 18 to 451, 19 to 451, or 20 to 451 of SEQ ID NO: 4.

EXAMPLES

The following examples are intended to illustrate, but not limit, the invention. Accordingly, from the above discussion and the Examples, one skilled in the art can ascertain essential characteristics of this disclosure, and without departing from the spirit and scope thereof, can make various changes and modifications to adapt to various uses and conditions.

Unless defined otherwise herein, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used with this disclosure.

Example 1. Expression of Zymogen of Tgase Variant (Pro-Tgase Variant) in *Escherichia coli*

A. Construction of Expression Plasmid for Expression of a Pro-Tgase Variant (SEQ ID NO:2)

The gene coding for the Pro-Tgase variant (i.e., zymogen form of Tgase variant) was codon optimized for expression in *E. coli* based on the published amino acid sequence (Kanaji, et al. (1993) J. Biol. Chem. 268(16):11565-11572), synthesized with an additional C-terminal His tag, and cloned into a pET vector operatively linked to the T7 promoter under control of the lacI repressor. The expression vector also contains the pMB1 origin of replication and a kanamycin resistance gene. The resulting plasmid was transformed first into *E. coli* DH-10B, using standard methods known in the art. The transformants were isolated by subjecting the cells to kanamycin selection, as known in the art (See, e.g., U.S. Pat. No. 8,383,346 and WO2010/144103, both of which are incorporated by reference herein, in their entirety), and the sequence of the Pro-Tgase gene was verified by Sanger sequencing. The plasmid was recovered from a positive clone, using methods known in the art, and transformed into *E. coli* BL21(DE3) for expression.

B. Expression and Isolation of Recombinant Pro-Tgase Variant (SEQ ID NO:2) in *E. coli*

The *E. coli* strain BL21(DE3), containing the Pro-Tgase expression vector, was cultured overnight in Luria broth at 37° C. until the culture reached saturation. The following morning, the culture was used to inoculate a shake flask containing a medium including glycerol, soy peptone, yeast extract, magnesium sulfate heptahydrate, and potassium phosphate monobasic, at 30-34° C. for up to 10 hours with continuous shaking. Isopropyl β-d-1-thiogalactopyranoside (IPTG) was added to a final concentration of 0.1-1 mM and incubation was continued at 20-25° C. for up to 24 hours.

Cells were harvested by centrifugation at 8000×g for up to 60 minutes. The supernatant was discarded, and the pellet was resuspended to 20% w/v in 50 mM tris(hydroxymethyl) aminomethane (Tris) HCl, pH 8. The cells were lysed using a high-pressure homogenizer at pressures from 15000-20000 psi. The crude lysates were clarified through centrifugation at 15000×g for up to 60 minutes. The clarified lysate containing Pro-Tgase was assessed by sodium dodecyl sulfate polyacrylamide gel electrophoresis (SDS-PAGE, FIG. 1) as described in Example 1D and by spectroscopy, and Tgase activity was assessed using the Colorimetric Activity Assay described in Example 1C.

Alternatively, the Pro-Tgase variant may be secreted, for example, from a microbial strain that is known to those skilled in the art to secrete Tgase such as *Streptomyces mobaraensis* or *Bacillus subtilis*. The pellet is discarded and the supernatant is recovered and is assessed by SDS-PAGE as described in Example 1D and by spectroscopy. Tgase activity is assessed using the Colorimetric Activity Assay described in Example 1C.

C. Colorimetric Activity Assay

Tgase activity was measured herein using a colorimetric hydroxamate activity assay (Folk and Cole (1965) J Biol Chemistry 240(7):2951-2960). Briefly, the hydroxamate assay uses N-benzyloxycarbonyl-L-glutaminyl-glycine (ZQG) as a low molecular weight amine acceptor substrate and hydroxylamine as an amine donor. In the presence of catalytically active Tgase, the hydroxylamine is incorporated to form Z-glutamylhydroxamate-glycine, which develops a colored complex with iron (III), detectable at 525 nm after incubation at 37° C. for 5-60 minutes. The calibration was performed using L-glutamic acid gamma-monohydroxamate (Millipore® Sigma®) as standard. One unit of Tgase is defined as the amount of enzyme that catalyzes formation of 1 μmol of the peptide derivative of gamma-glutamylhydroxylamine per minute.

D. SDS-PAGE Gel

This technique is used to assess the level of activation of a Pro-Tgase variant (SEQ ID NO:2) by TAMEP (see Example 3) and to analyze the molecular weight of expressed proteins. Mature Tgase was secured from commercial sources (Moo Gloo TI formula, Ajinomoto®) and used as a molecular weight standard for SDS-PAGE analysis (FIG. 1. Lane 1).

A 10 μg aliquot of the proteolytic cleavage product or expressed protein was added to Novex™ Bolt™ LDS Sample Buffer and Novex™ Bolt™ Sample Reducing Agent, mixed as directed, heated at 95° C. for 5 minutes, and then run on a 4-12% SDS-PAGE gel (Invitrogen™ NuPAGE™ 4-12% Bis-Tris Gel) for 30 minutes at 170 volts. Gels were stained with SimplyBlue™ Safe Stain (Invitrogen™) for 30-60 minutes before being destained in deionized water and photographed.

Example 2. Purification of Pro-Tgase Variant (SEQ ID NO:2) or FRAP-Tgase Variant (SEQ ID NO:5)

This method was used to purify either Pro-Tgase variant (SEQ ID NO:2) (as prepared in Example 1) or FRAP-Tgase variant (SEQ ID NO:5). FRAP-Tgase variant (SEQ ID NO:5) was prepared by incubating lysate containing Pro-Tgase variant (SEQ ID NO:2) with supernatant containing TAMEP (Example 3, loading at 1% vol) at 37° C. for 60 minutes.

2-(N-morpholino) ethanesulfonic acid (MES) was used to reduce the pH of the lysate to pH 5-6. This mixture was then clarified by centrifugation at 4000 g for 10-20 minutes. This clarified lysate was then loaded onto an SP Sepharose column (Cytiva®) that had been previously washed with water (10 column volumes) and then equilibrated with 25 mM MES buffer, pH 5.5 (10 column volumes), in accordance with the manufacturer's specifications. After the lysate flowed through the column at 1 mL/min, it was washed with 25 mM MES, pH 5.5 containing 50 mM sodium chloride (10 column volumes). The pro-Tgase variant (SEQ ID NO:2) or FRAP-Tgase variant (SEQ ID NO:5) was then eluted with 25 mM MES buffer, pH 5.5 containing 1 M sodium chloride (3 column volumes). Tgase activity was assessed using the Colorimetric Activity Assay described in Example 10. The Pro-Tgase variant (SEQ ID NO:2) did not show activity above baseline in the Colorimetric Activity Assay. Only activated forms of Tgases, for example, FRAP-Tgase variant (SEQ ID NO:5), showed activity in this assay.

The N-terminal peptide sequence of the FRAP-Tgase variant (SEQ ID NO:5) was confirmed using N-terminal sequencing. The technique of N-terminal sequencing was used to assess the level of activation of Pro-Tgase variant (SEQ ID NO:2) by TAMEP or FRAP-Tgase (SEQ ID NO:5) by TAP, such as SM-TAP.

This technique was used to determine the N-terminal sequence of a protein. An aliquot of protein (10 μg), i.e., FRAP-Tgase variant (SEQ ID NO:5), was added to commercial SDS-PAGE sample buffer (Novex™ Bolt™ LDS Sample Buffer and Novex™ Bolt™ Sample Reducing Agent, mixed as directed) and heated at 95° C. for 5 minutes. The sample was then electroporated through a 4-12% SDS-PAGE (Invitrogen™ NuPAGE™ 4-12% Bis-Tris Gel) gel at 170 volts for 30 minutes. The SDS-PAGE gel was then washed with water and transferred to a 0.45 um PVDF membrane using a Mini Blot Module (Invitrogen™) run at 20 volts for 60 minutes, in accordance with the manufacturer's instructions. This membrane was then stained with SimplyBlue™ Safe Stain (Invitrogen™) until clear protein bands were visible. Following washes with deionized water, protein bands corresponding to the proper molecular weight of FRAP-Tgase variant (SEQ ID NO:5) were excised and sent to the Protein Facility of the Iowa State University Office of Biotechnology for N-terminal sequencing analysis, where Edman Degradation analysis was used to determine the first 4-5 amino acids of the protein.

Example 3. Expression of Zymogen Forms, and Isolation of Catalytically Active Forms, of TAMEP and SM-TAP A. Expression of the Zymogen Forms of TAMEP (SEQ ID NO:3) and Zymogen Form of SM-TAP (SEQ ID NO:4) and Isolation of the Mature, Catalytically Active Forms of TAMEP and SM-TAP Genes encoding the wild-type *S. mobaraensis* Tgase proteases, transglutaminase activating metalloprotease (TAMEP) and *S. mobaraensis* tripeptidyl aminopeptidase (SM-TAP), were synthesized by Integrated DNA Technologies (Coralville, IA). Expression constructs for TAMEP and SM-TAP were designed with an N-terminal SacB signal sequence and hexa-His tag, and cloned using methods well known in the art. *B. subtilis* SCK6 delta-AlaR purchased from Bio-Technical Resources (Manitowoc, WI) were grown overnight at 37° C. in 5 mL of LB medium supplemented with 40 mg/mL D-alanine. The following day, the culture was diluted to an OD600 of 1.0 and xylose was added to a final concentration of 1%. After 2 hours, 250 μL of glycerol and ligated DNA was added and the culture tube was returned to the incubator for an additional 90 minutes. Following incubation, 10-1000 μL of culture was spread onto LB agar plates. Plates were grown at 37° C. overnight. The following day, 2-8 colonies were selected from each plate and inoculated into 3 mL of LB broth. Cultures were incubated at 37° C. for 48 hours and supernatant samples were taken periodically. SDS-PAGE was used to confirm secretion of the mature, catalytically active form of the enzyme into the media as determined by molecular weight. The expected molecular weight of the mature, catalytically active TAMEP is about 56 kDa and for the mature, catalytically active SM-TAP is about 50 kDa. It appeared that the mature, catalytically active form of each protease was formed from the zymogen form by constitutive processes such as an endogenous protease activity. Both mature, catalytically active proteases, TAMEP and SM-TAP, were isolated from their respective cell cultures by centrifugation at 8000×g for 10 minutes. The supernatant was used as isolated without further purification.

B. TAMEP Activity Assay

The activity of TAMEP from Example 3A above was determined using the following assay. Soluble TAMEP was added at 1% vol to purified Pro-Tgase variant (Example 2, 500 μL at 5 g/L). The reactions were then incubated at 37° C., 300 rpm, with time points being taken between 1-120 minutes. At each time point, a sample of the supernatant was removed and quenched with ethylenediaminetetraacetic acid (EDTA). Samples were then analyzed by ultra-performance liquid chromatography coupled to mass spectrometry (UPLC-MS, Thermo Scientific™ Vanquish™ UPLC and Thermo Scientific™ ISQ™ EM MS) to determine the total ion counts of pro-peptide cleaved off by TAMEP from the Pro-Tgase variant (SEQ ID NO:2), i.e., pro-peptide without FRAP tetrapeptide. Samples were run on an Accucore™ Vanquish™ C18 column (50 mm×2.1 mm ID, 1.5 μm particle size, Thermo Scientific™) on a linear gradient from 5% to 90% of 0.1% formic acid in acetonitrile over 1.5 minutes. N-terminal peptide sequencing, performed as described in Example 2 above, confirmed that the FRAP amino acid sequence was present on the N-terminal end of the catalytically active, not mature FRAP-Tgase variant (SEQ ID NO:5).

C. SM-TAP Activity Assay

The activity of SM-TAP from Example 3A above was determined using the following assay. Soluble SM-TAP was added at 1% vol to purified FRAP-Tgase variant (Example 2, 500 μL at 5 g/L). The reactions were then incubated at 37° C., 300 rpm, with time points collected from 1-120 minutes. At each time point a sample of the supernatant was removed and quenched with phenylmethylsulfonyl fluoride (PMSF). Samples were analyzed by ultra-performance liquid chromatography coupled to mass spectrometry (U PLC-MS, Thermo Scientific™ Vanquish™ UPLC and Thermo Scientific™ ISQ™ EM MS) to determine the total area count of FRAP tetrapeptide produced by the cleavage of FRAP-Tgase variant (SEQ ID NO:5) by SM-TAP. Samples were run on an Accucore™ Vanquish™ C18 column (50 mm×2.1 mm ID, 1.5 μm particle size, Thermo Scientific™) on a linear gradient from 5 to 90% of 0.1% formic acid in acetonitrile over 1.5 minutes. N-terminal peptide sequencing, performed as described in Example 2 above, confirmed that the FRAP tetrapeptide had been removed from the N-terminal end of the FRAP-Tgase variant (SEQ ID NO:5) resulting in a mature, catalytically active Tgase variant (SEQ ID NO:6).

Example 4. Immobilization of Mature, Catalytically Active Protease(s) onto Porous Solid Supports A. Protease Immobilization onto Covalent Porous Solid Supports The following procedure describes TAMEP (Example 3A) and/or SM-TAP (Example 3A) immobilization onto IB-COV-1, IB-COV-2, IB-COV-3, ANI-1 (modified for covalent binding), ECR8204F, ECR8209F, and ECR8215F.

Each porous solid support was weighed into a separate glass vial then washed with water (10 mL, 4×). The porous solid supports were then washed with 50 mM phosphate buffer adjusted to pH 8 (two porous solid support volumes, 4×).

ANI-1 porous solid support was modified for covalent binding by washing (4 porous solid support volumes, 1×) with a freshly prepared 1% glutaraldehyde solution in 50 mM phosphate buffer, pH 8, for 1 hour at 20° C. The glutaraldehyde solution was then removed and the porous solid support was washed (two porous solid support volumes, 4×) with 50 mM phosphate buffer, pH 8.

For all covalent porous solid supports, *B. subtilis* supernatant(s) containing TAMEP and/or SM-TAP (0.2-0.5 g/L) was then incubated on the porous solid support for 18-20 hours at 20° C., 700 rpm at 4:1 supernatant volume to porous solid support mass. The agitation was halted, and the protease(s) incubated on the porous solid support for an additional 2 hours. The supernatant was then removed from the porous solid support and then the porous solid support was washed with 50 mM phosphate buffer adjusted to pH 8 (4 porous solid support volumes, 1×). The porous solid supports were then washed with 50 mM phosphate buffer, pH 8, containing 500 mM sodium chloride (4 porous solid support volumes, 2×).

B. Immobilization of TAMEP onto Ionic Porous Solid Supports

The following procedure describes TAMEP (Example 3A) immobilization onto IB-CAT-1, IB-ANI-1 (unmodified), IB-ANI-2, IB-ANI-3, IB-ANI-4.

Each porous solid support was weighed into a separate glass vial then washed with water (10 mL, 4×). The porous solid supports were then washed with 50 mM phosphate buffer adjusted to pH 7 (two porous solid support volumes, 4×). *B. subtilis* supernatant containing TAMEP (0.2-0.5 g/L) was then incubated on the porous solid support for 18-20 hours at 20° C., 700 rpm at 4:1 supernatant volume to porous solid support mass. The agitation was halted, and the supernatant incubated on the porous solid support for an additional 2 hours. The supernatant was then removed from the porous solid support and then the porous solid support was washed with 50 mM phosphate buffer adjusted to pH 7 (4 porous solid support volumes, 4×).

C. Immobilization of SM-TAP onto Ionic Porous Solid Supports

The following procedure describes SM-TAP (Example 3A) immobilization onto IB-CAT-1, IB-ANI-1 (unmodified), IB-ANI-2, IB-ANI-3, IB-ANI-4.

Each porous solid support was weighed into a separate glass vial then washed with water (10 mL, 4×). The porous solid supports were then washed with 50 mM carbonate buffer adjusted to pH 10.5 (two porous solid support volumes, 4×). *B. subtilis* supernatant(s) containing TAMEP and/or SM-TAP (0.2-0.5 g/L) was then incubated on the porous solid support for 18-20 hours at 20° C., 700 rpm at 4:1 supernatant volume to porous solid support mass. The agitation was halted, and the protease(s) incubated on the porous solid support for an additional 2 hours. The supernatant was then removed from the porous solid support and then the porous solid support was washed with 50 mM carbonate buffer adjusted to pH 10.5 (4 porous solid support volumes, 4×).

D. Co-Immobilization of TAMEP and SM-TAP onto Ionic Porous Solid Supports

TAMEP and SM-TAP were co-immobilized onto IB-CAT-1, IB-ANI-1 (unmodified), IB-ANI-2, IB-ANI-3, IB-ANI-4 using the same protocol described in Example 4C above.

E. Protease Immobilization onto Adsorption Porous Solid Supports

The following procedure describes TAMEP (Example 3A) and/or SM-TAP (Example 3A) immobilization onto IB-ADS-1, IB-ADS-2, IB-ADS-3, and IB-ADS-4.

Each porous solid support was weighed into a separate glass vial then washed with water (10 mL, 4×). The porous solid supports were then washed with 50 mM phosphate buffer adjusted to pH 8 (two porous solid support volumes, 4×). *B. subtilis* supernatant(s) containing TAMEP and/or SM-TAP (0.2-0.5 g/L) was then incubated on the porous solid support for 18-20 hours at 20° C., 700 rpm at 4:1 supernatant volume to porous solid support mass. The agitation was halted, and the protease(s) incubated on the porous solid support for an additional 2 hours. The supernatant was then removed from the porous solid support and then the porous solid support was washed with 50 mM phosphate buffer adjusted to pH 8 (4 porous solid support volumes, 4×).

TABLE 2

Porous solid supports tested for separate immobilization of TAMEP and SM-TAP. TAMEP and SM-TAP retained activity when immobilized onto all supports listed.

| Porous solid support | Source | Type | Functional group | Matrix |
|---|---|---|---|---|
| IB-COV-1 | Chiralvision | Covalent, apolar | epoxide, butyl | Polyacrylic |
| IB-COV-2 | Chiralvision | Covalent, polar | epoxide | Polyacrylic |
| IB-COV-3 | Chiralvision | Covalent, polar | epoxide | Polyacrylic |
| IB-ADS-1 | Chiralvision | Adsorption, apolar | Alkyl | Polyacrylic |
| IB-ADS-2 | Chiralvision | Adsorption, apolar | Phenyl | Styrene |
| IB-ADS-3 | Chiralvision | Adsorption, apolar | Octadecyl | Methacrylate |
| IB-ADS-4 | Chiralvision | Adsorption, polar | Phenyl, methyl | Styrene |
| IB-CAT-1 | Chiralvision | Cationic, strong | Sulphonic | Styrene |
| IB-ANI-1 | Chiralvision | Anionic, apolar | primary amine | Polyacrylic |
| IB-ANI-2 | Chiralvision | Anionic, weak | Tertiary amine | Polystyrene |
| IB-ANI-3 | Chiralvision | Anionic, weak | Quaternary amine | Polystyrene |
| IB-ANI-4 | Chiralvision | Anionic, strong | Quaternary amine | Polystyrene |
| ECR8204F | Purolite ® | Covalent, polar | Epoxide | Methacrylate |
| ECR8209F | Purolite ® | Covalent, polar | Epoxide | Methacrylate |
| ECR8215F | Purolite ® | Covalent, polar | Epoxide | Methacrylate |

Example 5. Detection of Immobilized TAMEP Proteolytic Digestion

This example shows the activation of purified Pro-Tgase variant (SEQ ID NO:2), i.e., zymogen form of the Tgase variant. Both purified Pro-Tgase variant (SEQ ID NO:2) and clarified lysate containing Pro-Tgase (SEQ ID NO:2) performed similarly in all studies. For simplicity, protease activation of purified Pro-Tgase (SEQ ID NO:2) is presented herein.

TAMEP (Example 3A) immobilized on a porous solid support (20 mg, as prepared in Example 4) was added into a 1.5 mL glass vial. Then, purified Pro-Tgase variant (200 μL at 5 g/L, SEQ ID NO:2, as described in Example 2 above) was added to each vial. The vials were then incubated at 37° C., 700 rpm, with time points being taken between 1-120 minutes. At each time point, a sample of the supernatant was removed and quenched with EDTA. Samples were then analyzed as described in Example 3B. Tgase activity was assessed using the Colorimetric Activity Assay described in Example 10. N-terminal peptide sequencing, as performed in Example 2, confirmed that the FRAP tetrapeptide was present on the catalytically active, not mature FRAP-Tgase variant (SEQ ID NO:5). Activity assay results showed that TAMEP retained protease activity when immobilized on all the porous solid supports shown in Table 2.

Example 6. Detection of Immobilized SM-TAP Proteolytic Digestion

This example shows the activation of purified FRAP-Tgase variant, (SEQ ID NO:5). Both purified FRAP-Tgase variant (SEQ ID NO:5) and clarified lysate containing FRAP-Tgase (SEQ ID NO:5) performed similarly in all studies. For simplicity, protease activation of purified FRAP-Tgase (SEQ ID NO:5) is presented herein.

SM-TAP (Example 3A) immobilized on a porous solid support (20 mg porous solid support, as prepared in Example 4) was added to a 1.5 mL glass vial. Then, purified FRAP-Tgase variant (200 μL at 5 g/L, SEQ ID NO:5, as described in Example 2 above) was added into each vial. The vials were then incubated at 20° C., 700 rpm, with time points collected from 1-120 minutes. At each time point a sample of the supernatant was removed and quenched with PMSF. Samples were analyzed as described in Example 3C. Tgase activity was assessed using the Colorimetric Activity Assay described in Example 10 above. N-terminal peptide sequencing, performed as described in Example 2 above, showed that the FRAP tetrapeptide had been removed from the N-terminal end of the FRAP-Tgase variant (SEQ ID NO:5), resulting in the thermostable mature, catalytically active Tgase variant (SEQ ID NO:6). Activity assay results showed that SM-TAP retained protease activity when immobilized on all the porous solid supports shown in Table 2.

Example 7. Detection of Proteolytic Digestion by Co-Immobilized TAMEP and SM-TAP This example shows the activation of purified Pro-Tgase variant, (SEQ ID NO:2), i.e., zymogen form of the Tgase variant. Both purified Pro-Tgase variant (SEQ ID NO:2) and clarified lysate containing Pro-Tgase (SEQ ID NO:2) performed similarly in all studies. For simplicity, protease activation of purified Pro-Tgase (SEQ ID NO:2) is presented herein.

Top performing porous solid supports under the conditions described in Examples 5 and 6 above were selected for co-immobilization.

A porous solid support co-immobilized with TAMEP and SM-TAP (20 mg), as prepared in Example 4 above was added into a 1.5 mL glass vial. Then, purified Pro-Tgase variant (200 μL at 5 g/L, SEQ ID NO:2, described in Example 2 above) was added to the vial. The vials were then incubated at 20° C., 700 rpm, with time points collected from 1-120 minutes. At each time point a sample of the supernatant was removed and quenched with PMSF and EDTA. Samples were then analyzed as described in Example 3C. FRAP tetrapeptide will only be produced if TAMEP first cleaves the pro-peptide from Pro-Tgase variant (SEQ ID NO:2) then SM-TAP cleaves the FRAP tetrapeptide from the resulting FRAP-Tgase variant (SEQ ID NO:5). Tgase activity was assessed using the Colorimetric Activity Assay described in Example 10. N-terminal peptide sequencing, performed as described in Example 2, confirmed that FRAP had been removed from the N-terminal end of the FRAP-Tgase variant (SEQ ID NO:5) to produce a mature, catalytically active Tgase variant (SEQ ID NO:6). Activity assay results showed that co-immobilized TAMEP and SM-TAP retained protease activity on all the porous solid supports set forth in Table 3 below.

TABLE 3

A selection of the porous solid supports from Table 2 were tested for co-immobilization of TAMEP and SM-TAP. TAMEP and SM-TAP retained activity on all the porous solid supports shown below.

| Porous solid support | Source | Type | Functional group | Matrix |
|---|---|---|---|---|
| IB-COV-2 | Chiralvision | Covalent, polar | epoxide | Polyacrylic |
| IB-COV-3 | Chiralvision | Covalent, polar | epoxide | Polyacrylic |
| IB-ADS-1 | Chiralvision | Adsorption, apolar | Alkyl | Polyacrylic |
| IB-ADS-3 | Chiralvision | Adsorption, apolar | Octadecyl | Methacrylate |
| IB-ADS-4 | Chiralvision | Adsorption, polar | Phenyl, methyl | Styrene |
| IB-CAT-1 | Chiralvision | Cationic, strong | Sulphonic | Styrene |
| IB-ANI-2 | Chiralvision | Anionic, weak | Tertiary amine | Polystyrene |
| ECR8209F | Purolite ® | Covalent, polar | Epoxide | Methacrylate |
| ECR8215F | Purolite ® | Covalent, polar | Epoxide | Methacrylate |

Example 8. Determination of Activities of TAMEP and TAP

The same TAMEP and SM-TAP concentrations were used in both soluble and immobilized form.

Unless otherwise indicated, all TAMEP and SM-TAP concentrations are based on total protein.

A. Determination of Combined Activity of Soluble TAMEP (not Immobilized) and Soluble SM-TAP (not Immobilized)

Purified Pro-Tgase variant (SEQ ID NO:2, 250 μL at 5 g/L) was added to a 1.5 mL glass vial containing soluble TAMEP (0.1 mg, not immobilized) and soluble SM-TAP (0.1 mg, not immobilized). Samples were analyzed in the same manner as in Example 3C.

B. Determination of Combined Activity of Soluble TAMEP (not Immobilized) and SM-TAP Immobilized on IB-COV-3

Purified Pro-Tgase variant (SEQ ID NO:2, 250 μL at 5 g/L) was added into 1.5 mL glass vial containing soluble TAMEP (0.1 mg, not immobilized) and immobilized SM-TAP (10 mg porous solid support, 0.1 mg SM-TAP). Samples were analyzed in the same manner as described in Example 3C above.

C. Determination of Combined Activity of TAMEP Immobilized on IB-COV-1 and Soluble SM-TAP (not Immobilized)

Purified Pro-Tgase variant (SEQ ID NO:2, 250 μL at 5 g/L) was added into a 1.5 mL glass vial containing immobilized TAMEP (10 mg porous solid support, 0.1 mg TAMEP) and soluble SM-TAP (0.1 mg, not immobilized). Samples were analyzed in the same manner as described in Example 3C above.

D. Determination of Combined Activity of TAMEP Immobilized on IB-COV-1 and SM-TAP Immobilized on IB-COV-3

Purified Pro-Tgase variant (SEQ ID NO:2, 250 μL at 5 g/L) was added into a 1.5 mL glass vial containing separately immobilized TAMEP (10 mg porous solid support, 0.1 mg TAMEP) and SM-TAP (10 mg porous solid support, 0.1 mg SM-TAP). Samples were analyzed in the same manner as described in Example 3C above.

E. Determination of Combined Activity of TAMEP and SM-TAP Co-Immobilized on ECR8215F or IB-COV-3

Purified Pro-Tgase variant (SEQ ID NO:2, 250 μL at 5 g/L) was added into a 1.5 mL glass vial containing co-immobilized TAMEP and SM-TAP (20 mg porous solid support, 0.2 mg of TAMEP and SM-TAP, combined). Samples were analyzed in the same manner as described in Example 3C above.

It was found that co-immobilized TAMEP and SM-TAP outperformed soluble and separately immobilized TAMEP and SM-TAP. Specifically, the results showed an increase in FRAP total area counts by UPLC-MS (as described in Example 3C) when compared to the proteases in soluble form (not immobilized) or just one of TAMEP or TAP is immobilized and the other is in solution or immobilization onto separate porous solid supports. Results are set forth in Table 4 and FIG. 2.

Additionally, FIG. 2 shows that the most FRAP was produced by the co-immobilized TAMEP and SM-TAP when compared to the amount of FRAP produced by either TAMEP and SM-TAP immobilized separately or TAMEP and SM-TAP both in soluble form i.e., not immobilized. FIG. 2 also shows that more FRAP was produced by TAMEP and SM-TAP immobilized separately as compared to soluble TAMEP and SM-TAP over 120 minutes. In other words, co-immobilized TAMEP and SM-TAP and separately immobilized TAMEP and SM-TAP outperformed soluble TAMEP and SM-TAP.

TABLE 4

Determination of combined activities of TAMEP and SM-TAP as described in Examples 8A-8E.

| Immobilization status | Total FRAP area counts at 120 minutes |
|---|---|
| TAMEP and SM-TAP co-immobilized on ECR8215F-Purolite ® (Example 8E) | ++ |
| TAMEP and SM-TAP co-immobilized on IB-COV-3 Chiralvision (Example 8E) | ++ |
| TAMEP immobilized on IB-COV-1 and SM-TAP immobilized IB-COV-3 (Example 8D) | + |
| TAMEP immobilized on IB-COV-1 + SM-TAP in solution (Example 8C) | + |
| SM-TAP immobilized on IB-COV-3 + TAMEP in solution (Example 8B) | − |
| TAMEP in solution and SM-TAP in solution (not immobilized) (Example 8A) | − |

++ denotes a >2-fold increase in FRAP production compared to soluble (not immobilized) TAMEP and SM-TAP,
+ denotes a 1.5 to 2-fold increase in FRAP production, and
− denotes <1.5-fold increase in FRAP production as determined by UPLC-MS total area counts (as performed in Example 3C).

Amino Acid Sequences

SEQ ID NO:1 Wild-type *Streptomyces mobaraensis* Tgase zymogen (Pro-Tgase). Leader sequence (pro-) is denoted in bold, underlined text.

DNGAGEETKSYAETYRLTADDVANINALNESAPAASSAGPSFRAPDSDDR

VTPPAEPLDRMPDPYRPSYGRAETVVNNYIRKWQQVYSHRDGRKQQMTEE

QREWLSYGCVGVTWVNSGQYPTNRLAFASFDEDRFKNELKNGRPRSGETR

AEFEGRVAKESFDEEKGFQRAREVASVMNRALENAHDESAYLDNLKKELA

-continued

NGNDALRNEDARSPFYSALRNTPSFKERNGGNHDPSRMKAVIYSKHFWSG

QDRSSSADKRKYGDPDAFRPAPGTGLVDMSRDRNIPRSPTSPGEGFVNFD

YGWFGAQTEADADKTVWTHGNHYHAPNGSLGAMHVYESKFRNWSEGYSDF

DRGAYVITFIPKSWNTAPDKVKQGWP

SEQ ID NO:2 A thermostable variant of *Streptomyces mobaraensis* Tgase in zymogen form with two methionine amino acid residues—one methionine is located at the N-terminus of the Pro-sequence and the second methionine is located between the Pro-sequence and the N-terminus of the mature domain (Pro-Tgase variant). Leader sequence (pro-) is denoted in bold, underlined text.

MDNGAGEETKSYAETYRLTADDVANINALNESAPAASSAGPSFRAPMDPD

DRVTPPAEPLDRMPDPYRPSYGRAETVVNNYIRKWQQVYSHRDGRKQQMT

EEQREWLSYGCVGVTWVNSGQYPTNRLAFASFDEDRFKNELKNGRPRSGE

TRAEFEGRVAKESFDEEKGFQRAREVASVMNRALENAHDESAYLDNLKKE

LANGNDALRNEDARSPFYSALRNTPSFKERNGGNHDPSRMKAVIYSKHFW

SGQDRSSSADKRKYGDPDAFRPAPGTGLVDMSRDRNIPRSPTSPGEGFVN

FDYGWFGAQTEADADKTVWTHGNHYHAPNGSLGAMHVYESKFRNWSEGYS

DFDRGAYVITFIPKSWNTAPDKVKQGWP

SEQ ID NO:3 Wild-type *Streptomyces mobaraensis* transglutaminase-activating M4 metalloprotease (TAMEP) in zymogen form with the native signal peptide deleted and a leading methionine included to facilitate recombinant expression. Putative leader sequence (pro-) is denoted in bold, underlined text.

MGQDKAAHPAPRQSIHKPDPGAEPVKLTPSQRAELIRDANATKAETAKNL

GLGAKEKLVVKDVVKDKNGTLHTRYERTYDGLPVLGGDLVVDATRSGQVK

TAAKATKQRIAVASTTPSLAASAAEKDAVKAARAKGSKAGKADKAPRKVV

WAAKGTPVLAYETVVGGVQDDGTPSQLHVITDAKTGKKLFEFQGVKQGTG

NSQHSGQVQIGTTKSGSSYQMNDTTRGGHKTYNLNHGSSGTGTLFTDSDD

VWGNGTNSDPATAGVDAHYGAQLTWDYYKNVHGRNGIRGDGVGAYSRVHY

GNNYVNAFWDDSCFCMTYGDGNGIPLTSIDVAAHEMTHGVTSATANLTYS

GESGGLNEATSDMMATAVEFWANNPADPGDYLIGEKININGDGTPLRYMD

KPSKDGASKDAWYSGLGGIDVHYSSGPANHWFYLASEGSGPKDIGGVHYD

SPTSDGLPVTGVGRDNAAKIWFKALTERMQSNTDYKGARDATLWAAGELF

GVNSDTYNNVANAWAAINVGPRASSGVSVTSPGDQTSIVNQAVSLQIKAT

GSTSGALTYSATGLPAGLSINASTGLISGTPTTTGTSNVTVTVKDSAGKT

GSTSFKWTVNTTGGGSVFENTTQVAIPDAGAAVTSPIVVTRSGNGPSALK

VDVNITHTYRGDLTIDLVAPNGKTWRLKNSDAWDSAADVSETYTVDASSV

SANGTWKLKVQDVYSGDSGTIDKWRLTF

SEQ ID NO:4 Wild-type *Streptomyces mobaraensis* transglutaminase-activating tripeptidyl aminopeptidase (SM-TAP) in zymogen form with the native signal peptide deleted and a leading methionine included to facilitate recombinant expression. Putative leader sequence (pro-) is denoted in bold, underlined text.

MASITAPQADIKDRILKIPGMKFVEEKPYQGYRYLVMTYRQPVDHRNPGK

GTFEQRFTLLHKDTDRPTVFFTSGYNVSTNPSRSEPTRIVDGNQVSMEYR

FFTPSRPQPADWSKLDIWQAASDQHRLYQALKPVYGKNWLATGGSKGGMT

ATYFRRFYPNDMNGTVAYVAPNDVNDKEDSAYDKFFQNVGDKACRTQLNS

VQREALVRRDEIVARYEKWAKENGKTFKVVGSADKAYENVVLDLVWSFWQ

YHLQSDCASVPATKASTDELYKFIDDISGFDGYTDQGLERFTPYYYQAGT

QLGAPTVKNPHLKGVLRYPGINQPRSYVPRDIPMTFRPGAMADVDRWVRE

DSRNMLFVYGQNDPWSGEPFRLGKGAAARHDYRFYAPGGNHGSNIAQLVA

DERAKATAEVLKWAGVAPQAVQKDEKAAKPLAPFDAKLDRVKNDKQSALR

P

SEQ ID NO:5 A thermostable variant of *Streptomyces mobaraensis* Tgase having a FRAP tetrapeptide at the N-terminus of the mature domain with a methionine amino acid residue located between the FRAP tetrapeptide and N-terminus of the mature domain of the thermostable Tgase variant (FRAP-Tgase variant). Leader sequence (pro-) is denoted in bold, underlined text.

FRAPMDPDDRVTPPAEPLDRMPDPYRPSYGRAETVVNNYIRKWQQVYSHR

DGRKQQMTEEQREWLSYGCVGVTWVNSGQYPTNRLAFASFDEDRFKNELK

-continued

NGRPRSGETRAEFEGRVAKESFDEEKGFQRAREVASVMNRALENAHDESA

YLDNLKKELANGNDALRNEDARSPFYSALRNTPSFKERNGGNHDPSRMKA

VIYSKHFWSGQDRSSSADKRKYGDPDAFRPAPGTGLVDMSRDRNIPRSPT

SPGEGFVNFDYGWFGAQTEADADKTVWTHGNHYHAPNGSLGAMHVYESKF

RNWSEGYSDFDRGAYVITFIPKSWNTAPDKVKQGWP

SEQ ID NO: 6 A thermostable variant of *Streptomyces mobaraensis* Tgase with the FRAP tetrapeptide removed from the N-terminus of the mature domain of the thermostable Tase variant and a leading methionine amino acid residue is located at the N-terminus of the mature domain of the thermostable Tgase variant.

MDPDDRVTPPAEPLDRMPDPYRPSYGRAETVVNNYIRKWQQVYSHRDGRK

QQMTEEQREWLSYGCVGVTWVNSGQYPTNRLAFASFDEDRFKNELKNGRP

RSGETRAEFEGRVAKESFDEEKGFQRAREVASVMNRALENAHDESAYLDN

LKKELANGNDALRNEDARSPFYSALRNTPSFKERNGGNHDPSRMKAVIYS

KHFWSGQDRSSSADKRKYGDPDAFRPAPGTGLVDMSRDRNIPRSPTSPGE

GFVNFDYGWFGAQTEADADKTVWTHGNHYHAPNGSLGAMHVYESKFRNWS

EGYSDFDRGAYVITFIPKSWNTAPDKVKQGWP

What is claimed is:

1. A transglutaminase-activating M4 metalloprotease (TAMEP) and a tripeptidyl aminopeptidase (TAP) co-immobilized on a porous solid support, wherein higher transglutaminase activity is achieved when a microbial transglutaminase or variant thereof is activated by using the co-immobilized TAMEP and TAP compared to using the TAMEP and the TAP separately immobilized on the porous solid support, and wherein the TAMEP is from *Streptomyces mobaraensis* and the TAP is from *Streptomyces mobaraensis*.

2. A method for activating a zymogen form of a microbial transglutaminase or a variant thereof to produce a mature, catalytically active form of the microbial transglutaminase, the method comprising (a) co-immobilizing at least one transglutaminase-activating M4 metalloprotease (TAMEP) and at least one tripeptidyl aminopeptidase from (TAP) on the same porous solid support; and (b) contacting the zymogen form of the microbial transglutaminase with co-immobilized TAMEP and TAP to produce a mature, catalytically active form of the microbial transglutaminase;

wherein the TAMEP is from *Streptomyces mobaraensis* and the TAP is from *Streptomyces mobaraensis*; and wherein the method results in higher transglutaminase activity compared to using the TAMEP and the TAP separately immobilized on the porous solid support to activate the zymogen form of the microbial transglutaminase or variant thereof.

3. The method of claim 2 wherein the mature, catalytically active microbial transglutaminase is separated from the immobilized proteases.

* * * * *

SEQUENCE LISTING

```
Sequence total quantity: 6
SEQ ID NO: 1            moltype = AA  length = 376
FEATURE                 Location/Qualifiers
source                  1..376
                        mol_type = protein
                        organism = Streptomyces mobaraensis
SEQUENCE: 1
DNGAGEETKS YAETYRLTAD DVANINALNE SAPAASSAGP SFRAPDSDDR VTPPAEPLDR  60
MPDPYRPSYG RAETVVNNYI RKWQQVYSHR DGRKQQMTEE QREWLSYGCV GVTWVNSGQY  120
PTNRLAFASF DEDRFKNELK NGRPRSGETR AEFEGRVAKE SFDEEKGFQR AREVASVMNR  180
ALENAHDESA YLDNLKKELA NGNDALRNED ARSPFYSALR NTPSFKERNG GNHDPSRMKA  240
VIYSKHFWSG QDRSSSADKR KYGDPDAFRP APGTGLVDMS RDRNIPRSPT SPGEGFVNFD  300
YGWFGAQTEA DADKTVWTHG NHYHAPNGSL GAMHVYESKF RNWSEGYSDF DRGAYVITFI  360
PKSWNTAPDK VKQGWP                                                  376

SEQ ID NO: 2            moltype = AA  length = 378
FEATURE                 Location/Qualifiers
source                  1..378
                        mol_type = protein
                        organism = Streptomyces mobaraensis
SEQUENCE: 2
MDNGAGEETK SYAETYRLTA DDVANINALN ESAPAASSAG PSFRAPMDPD DRVTPPAEPL  60
DRMPDPYRPS YGRAETVVNN YIRKWQQVYS HRDGRKQQMT EEQREWLSYG CVGVTWVNSG  120
QYPTNRLAFA SFDEDRFKNE LKNGRPRSGE TRAEFEGRVA KESFDEEKGF QRAREVASVM  180
NRALENAHDE SAYLDNLKKE LANGNDALRN EDARSPFYSA LRNTPSFKER NGGNHDPSRM  240
KAVIYSKHFW SGQDRSSSAD KRKYGDPDAF RPAPGTGLVD MSRDRNIPRS PTSPGEGFVN  300
FDYGWFGAQT EADADKTVWT HGNHYHAPNG SLGAMHVYES KFRNWSEGYS DFDRGAYVIT  360
FIPKSWNTAP DKVKQGWP                                                378

SEQ ID NO: 3            moltype = AA  length = 728
FEATURE                 Location/Qualifiers
source                  1..728
                        mol_type = protein
                        organism = Streptomyces mobaraensis
SEQUENCE: 3
MGQDKAAHPA PRQSIHKPDP GAEPVKLTPS QRAELIRDAN ATKAETAKNL GLGAKEKLVV  60
KDVVKDKNGT LHTRYERTYD GLPVLGGDLV VDATRSGQVK TAAKATKQRI AVASTTPSLA  120
ASAAEKDAVK AARAKGSKAG KADKAPRKVV WAAKGTPVLA YETVVGGVQD DGTPSQLHVI  180
TDAKTGKKLF EFQGVKQGTG NSQHSGQVQI GTTKSGSSYQ MNDTTRGGHK TYNLNHGSSG  240
TGTLFTDSDD VWGNGTNSDP ATAGVDAHYG AQLTWDYYKN VHGRNGIRGD GVGAYSRVHY  300
```

-continued

```
GNNYVNAFWD DSCFCMTYGD GNGIPLTSID VAAHEMTHGV TSATANLTYS GESGGLNEAT  360
SDMMATAVEF WANNPADPGD YLIGEKININ GDGTPLRYMD KPSKDGASKD AWYSGLGGID  420
VHYSSGPANH WFYLASEGSG PKDIGGVHYD SPTSDGLPVT GVGRDNAAKI WFKALTERMQ  480
SNTDYKGARD ATLWAAGELF GVNSDTYNNV ANAWAAINVG PRASSGVSVT SPGDQTSIVN  540
QAVSLQIKAT GSTSGALTYS ATGLPAGLSI NASTGLISGT PTTTGTSNVT VTVKDSAGKT  600
GSTSFKWTVN TTGGGSVFEN TTQVAIPDAG AAVTSPIVVT RSGNGPSALK VDVNITHTYR  660
GDLTIDLVAP NGKTWRLKNS DAWDSAADVS ETYTVDASSV SANGTWKLKV QDVYSGDSGT  720
IDKWRLTF                                                          728

SEQ ID NO: 4            moltype = AA  length = 451
FEATURE                 Location/Qualifiers
source                  1..451
                        mol_type = protein
                        organism = Streptomyces mobaraensis
SEQUENCE: 4
MASITAPQAD IKDRILKIPG MKFVEEKPYQ GYRYLVMTYR QPVDHRNPGK GTFEQRFTLL  60
HKDTDRPTVF FTSGYNVSTN PSRSEPTRIV DGNQVSMEYR FFTPSRPQPA DWSKLDIWQA  120
ASDQHRLYQA LKPVYGKNWL ATGGSKGGMT ATYFRRFYPN DMNGTVAYVA PNDVNDKEDS  180
AYDKFFQNVG DKACRTQLNS VQREALVRRD EIVARYEKWA KENGKTFKVV GSADKAYENV  240
VLDLVWSFWQ YHLQSDCASV PATKASTDEL YKFIDDISGF DGYTDQGLER FTPYYYQAGT  300
QLGAPTVKNP HLKGVLRYPG INQPRSYVPR DIPMTFRPGA MADVDRWVRE DSRNMLFVYG  360
QNDPWSGEPF RLGKGAAARH DYRFYAPGGN HGSNIAQLVA DERAKATAEV LKWAGVAPQA  420
VQKDEKAAKP LAPFDAKLDR VKNDKQSALR P                                451

SEQ ID NO: 5            moltype = AA  length = 336
FEATURE                 Location/Qualifiers
source                  1..336
                        mol_type = protein
                        organism = Streptomyces mobaraensis
SEQUENCE: 5
FRAPMDPDDR VTPPAEPLDR MPDPYRPSYG RAETVVNNYI RKWQQVYSHR DGRKQQMTEE  60
QREWLSYGCV GVTWVNSGQY PTNRLAFASF DEDRFKNELK NGRPRSGETR AEFEGRVAKE  120
SFDEEKGFQR AREVASVMNR ALENAHDESA YLDNLKKELA NGNDALRNED ARSPFYSALR  180
NTPSFKERNG GNHDPSRMKA VIYSKHFWSG QDRSSSADKR KYGDPDAFRP APGTGLVDMS  240
RDRNIPRSPT SPGEGFVNFD YGWFGAQTEA DADKTVWTHG NHYHAPNGSL GAMHVYESKF  300
RNWSEGYSDF DRGAYVITFI PKSWNTAPDK VKQGWP                           336

SEQ ID NO: 6            moltype = AA  length = 332
FEATURE                 Location/Qualifiers
source                  1..332
                        mol_type = protein
                        organism = Streptomyces mobaraensis
SEQUENCE: 6
MDPDDRVTPP AEPLDRMPDP YRPSYGRAET VVNNYIRKWQ QVYSHRDGRK QQMTEEQREW  60
LSYGCVGVTW VNSGQYPTNR LAFASFDEDR FKNELKNGRP RSGETRAEFE GRVAKESFDE  120
EKGFQRAREV ASVMNRALEN AHDESAYLDN LKKELANGND ALRNEDARSP FYSALRNTPS  180
FKERNGGNHD PSRMKAVIYS KHFWSGQDRS SSADKRKYGD PDAFRPAPGT GLVDMSRDRN  240
IPRSPTSPGE GFVNFDYGWF GAQTEADADK TVWTHGNHYH APNGSLGAMH VYESKFRNWS  300
EGYSDFDRGA YVITFIPKSW NTAPDKVKQG WP                               332
```